United States Patent
Okada et al.

(10) Patent No.: US 8,845,114 B2
(45) Date of Patent: Sep. 30, 2014

(54) LIGHTING DEVICE FOR IMAGE CAPTURING IN ELECTRONIC COMPONENT MOUNTING APPARATUS

(75) Inventors: Yasuichi Okada, Kumamoto (JP);
Tadashi Endou, Fukuoka (JP);
Hirokazu Tanaka, Fukuoka (JP)

(73) Assignee: Panasonic Corporation, Osaka (JP)

( * ) Notice: Subject to any disclaimer, the term of this patent is extended or adjusted under 35 U.S.C. 154(b) by 948 days.

(21) Appl. No.: 12/523,334

(22) PCT Filed: Feb. 19, 2008

(86) PCT No.: PCT/JP2008/000274
§ 371 (c)(1),
(2), (4) Date: Jul. 16, 2009

(87) PCT Pub. No.: WO2008/114486
PCT Pub. Date: Sep. 25, 2008

(65) Prior Publication Data
US 2010/0118508 A1     May 13, 2010

(30) Foreign Application Priority Data

Feb. 21, 2007  (JP) .................................. 2007-40232
Feb. 21, 2007  (JP) .................................. 2007-40233

(51) Int. Cl.
*G03B 15/02*       (2006.01)
*H05K 13/04*       (2006.01)
*G01N 21/88*       (2006.01)

(52) U.S. Cl.
CPC ........ *G01N 21/8806* (2013.01); *H05K 13/0413* (2013.01); *G01N 2201/062* (2013.01)
USPC .......... 362/3; 362/234; 362/249.02; 362/253; 396/155; 396/175; 355/18; 355/40

(58) Field of Classification Search
USPC ................ 362/3, 230, 231, 234, 253, 249.02; 396/155, 175; 355/18, 40
See application file for complete search history.

(56) References Cited

U.S. PATENT DOCUMENTS 6,542,238 B1 * 4/2003 Tsuboi et al. ................. 356/401
7,461,944 B2 * 12/2008 Alessio .......................... 362/184

(Continued)

FOREIGN PATENT DOCUMENTS

EP      1 548 396 A1    6/2005
JP      04-241476       8/1992

(Continued)

OTHER PUBLICATIONS

International Search Report for PCT/JP2008/000274.

(Continued)

*Primary Examiner* — Mary McManmon
(74) *Attorney, Agent, or Firm* — Pearne & Gordon LLP

(57) ABSTRACT

To provide a lighting device for image capturing in an electronic component mounting apparatus that has small dimensions in the height direction and a small size in a plan view and thus can meet demands in a reduction in size.
In an electronic component mounting apparatus, a surface lighting unit 30 that emits illumination light to a substrate, which is an object whose image is to be captured by a camera 25, includes as a main component a flat lighting substrate 31 that is provided between the camera 25 and the substrate, which is an object whose image is to be captured, so as to be substantially parallel to the surface of the substrate. Upper illumination light sources 32a, intermediate illumination light sources 32b, and lower illumination light sources 32c are arranged around an opening 31a for image capturing on one surface of the lighting substrate 31 facing the substrate in this order from the inside to the outside, such that they emit illumination light components to the surface of the substrate at different emission angles. In this way, it is possible to reduce the dimensions of the surface lighting unit 30 in the height direction and thus meet demands for a reduction in size.

5 Claims, 10 Drawing Sheets

(56) References Cited

U.S. PATENT DOCUMENTS

| | | |
|---|---|---|
| 7,502,170 B2 * | 3/2009 | Nakano et al. .............. 359/627 |
| 2006/0067668 A1 * | 3/2006 | Kita .............................. 396/182 |

FOREIGN PATENT DOCUMENTS

| | | |
|---|---|---|
| JP | 08 219716 A | 8/1996 |
| JP | 09 033445 A | 2/1997 |
| JP | 2000-022393 | 1/2000 |
| JP | 2003-168899 A | 6/2003 |

OTHER PUBLICATIONS

Japanese Office action for JP2007-040232 dated Dec. 7, 2010.

* cited by examiner

Fig. 5-a
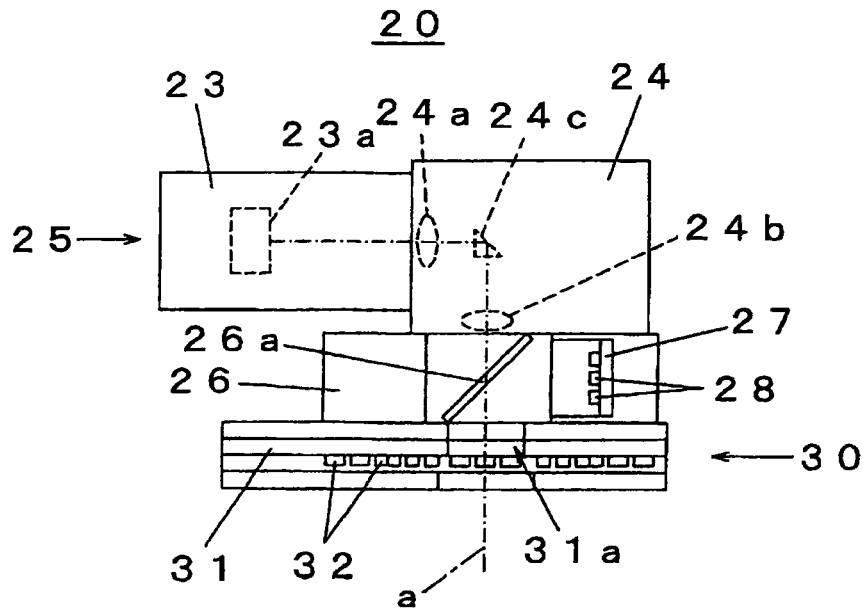
Fig. 5-b
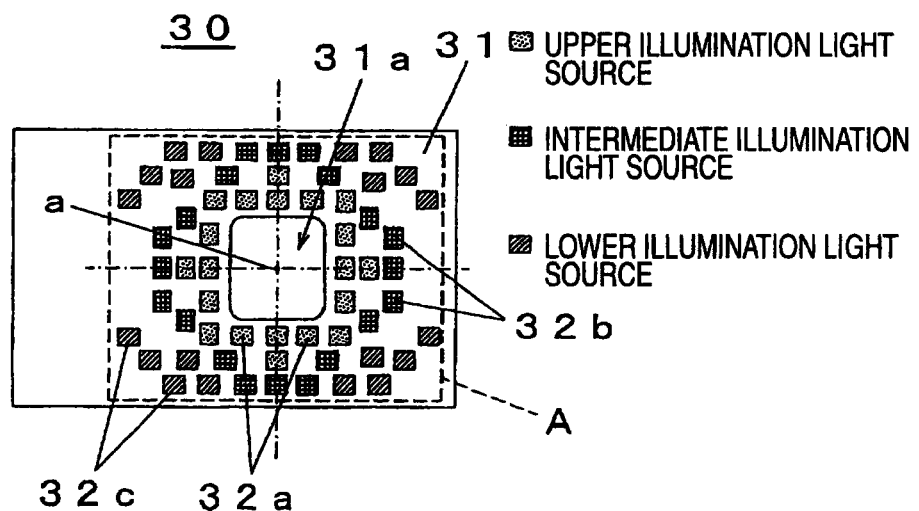

Fig. 8-a
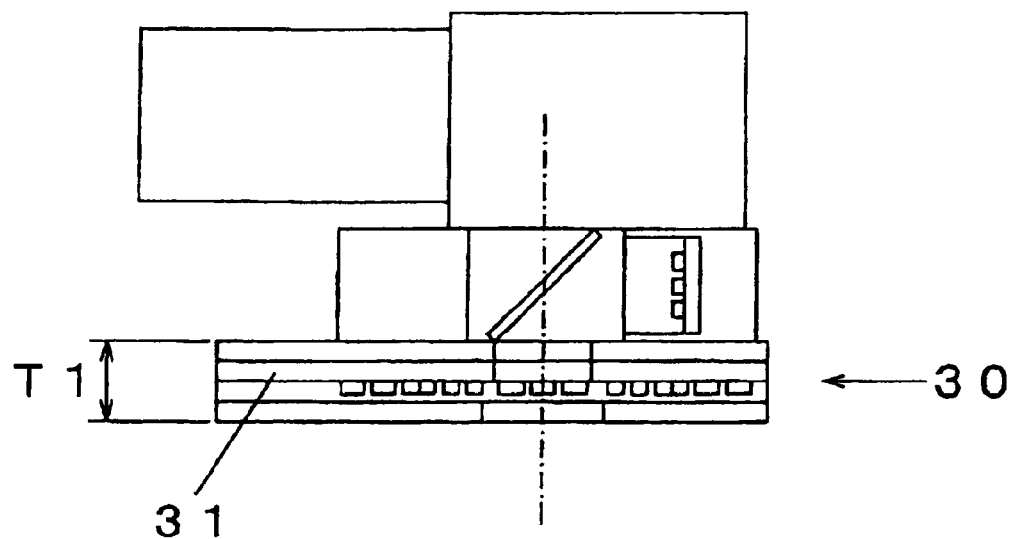

Fig. 8-b
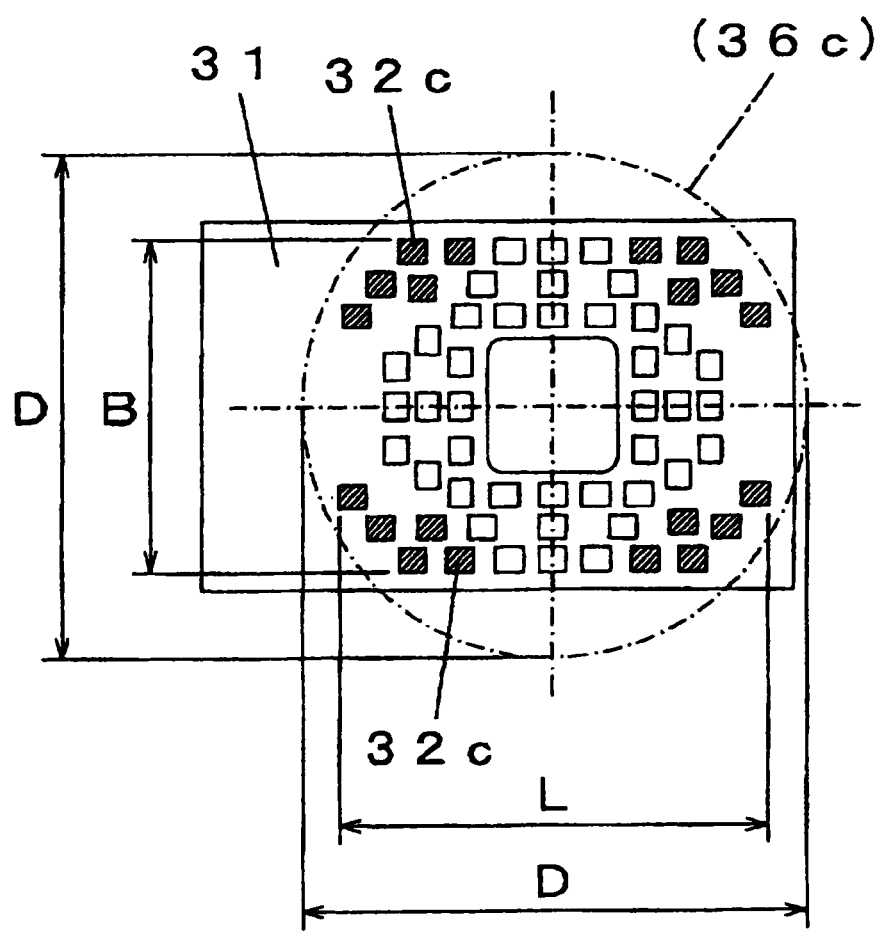

Fig. 9-a
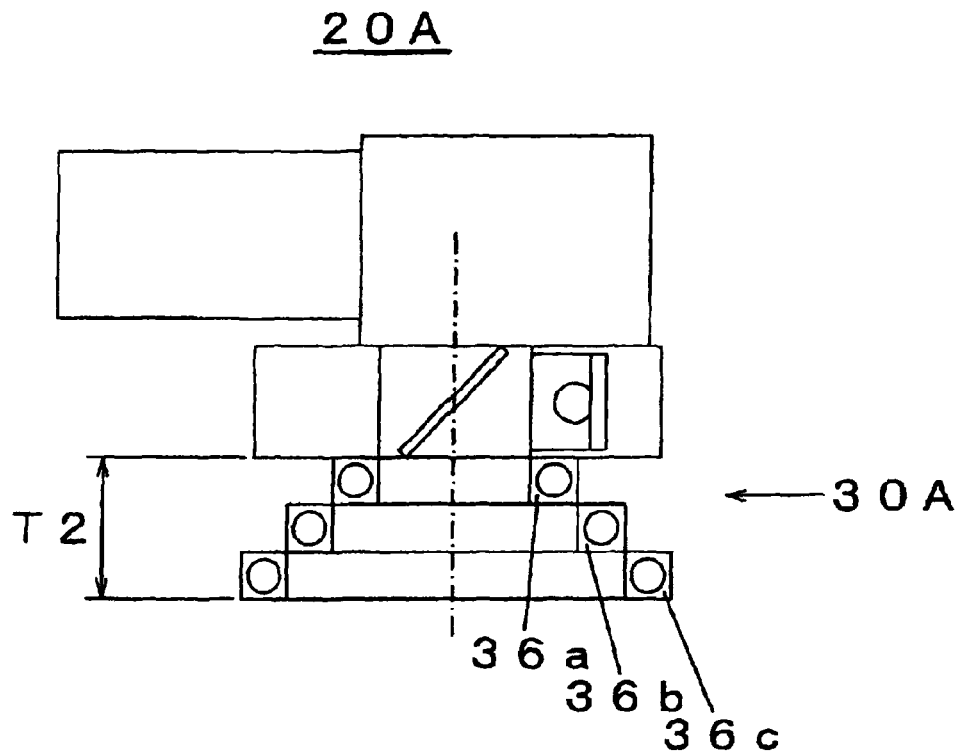
Fig. 9-b
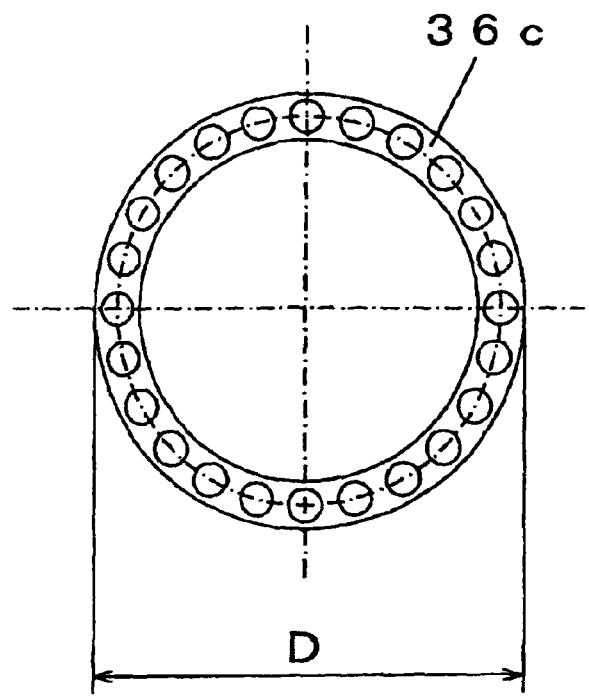

LIGHTING DEVICE FOR IMAGE CAPTURING IN ELECTRONIC COMPONENT MOUNTING APPARATUS

TECHNICAL FIELD

The present invention relates to a lighting device for image capturing that is used to capture the image of an object to be recognized in an electronic component mounting apparatus such as an electronic component placing apparatus that places electronic components on a substrate.

BACKGROUND ART

In electronic components mounting apparatuses, such as electronic component placing apparatuses used in electronic component mounting lines, in order to identify substrates or detect the positions of the substrates, a camera is used to capture the image of an object to be recognized, such as an identification mark provided on the surface of the substrate. During an image capturing process, a lighting device emits illumination light to the surface of the substrate, and a camera receives light reflected from an object to be recognized, thereby capturing the image of the object to be recognized.

In general, reflection characteristics of reflecting illumination light depend on the surface properties or states of objects to be recognized. Therefore, in order to enable the camera to receive good reflected light during an image capturing process, the following structure has been proposed in which a plurality of light sources forming a lighting device are disposed at different positions and the emission angle of illumination light to the surface of the substrate can be changed according to objects to be recognized (for example, see Patent Document 1). In the structure disclosed in Patent Document 1, a plurality of lighting substrates each having LEDs, serving as light sources, arranged in a ring shape thereon are laminated in the vertical direction, and thus the light sources emit illumination light components to the substrate, which is an object whose image is to be captured, at different emission angles in plural directions.

Patent Document 1
  JP-A-2003-168899

DISCLOSURE OF INVENTION

Technical Problem

In recent years, with a reduction in the sizes of electronic apparatuses and an improvement in the performances thereof, the size of a substrate to which electronic components are mounted has been decreased, and the mounting density of electronic components have been increased. Therefore, the size of mounting equipment for such a kind of substrate has been decreased, and demands for a reduction in the sizes of components used in an electronic component mounting apparatus that mounts electronics parts on a substrate have been made. For example, in a part mounting mechanism that takes out electronic components from a part supply unit and transports and mounts the electronic components on a substrate, the size of a mounting head in a plan view and the dimensions thereof in the height direction are more restricted than that according to the related art.

However, when a lighting device having the above-mentioned structure is used as the lighting device of the electronic component mounting apparatus having such a restriction in size, the dimensions of the lighting device in the height direction are larger than a height space that is allowable in the design of the apparatus, due to the base structure in which a plurality of lighting substrates are laminated in the vertical direction. In addition, the size of the lighting device in a plan view is larger than a space in a plan view that is allowable in the design of the apparatus, due to the light source structure in which a plurality of LEDs are arranged in a ring shape. For these reasons, it is difficult to reduce the dimensions of the lighting device in the height direction in the electronic component mounting apparatus according to the related art, due to the arrangement of light sources, and it is also difficult to reduce the size of the lighting device in a plan view due to the structure of light sources. As a result, it is difficult to apply the lighting device to an electronic component mounting device with a small size.

Accordingly, an object of the invention is to provide a light device for image capturing in an electronic component mounting apparatus that has small dimensions in the height direction and a small size in a plan view and can meet demands for a reduction in size.

Technical Solution

According to an aspect of the invention, there is provided a lighting device for image capturing that emits illumination light to a substrate whose image is to be captured by a camera in an electronic component mounting apparatus. The lighting device includes: a flat lighting substrate that is disposed between the substrate and the camera so as to be substantially parallel to the surface of the substrate, and has a light source portion provided on its one surface facing the substrate; and an illumination control unit that controls the light source portion. The light source portion includes a plurality of individual light sources that are arranged around an opening for image capturing through which an imaging optical axis of the camera passes and emit the illumination light to the surface of the substrate at different emission angles. The illumination control unit individually controls the plurality of individual light sources.

Advantageous Effects

According to the invention, a plurality of individual light sources that emit illumination light components to the surface of a substrate at different emission angles are arranged on a flat lighting substrate. According to this structure, it is possible to reduce the dimensions of a lighting device in the height direction and the size thereof in a plan view. As a result, it is possible to meet demands for a reduction in the size of the lighting device.

BRIEF DESCRIPTION OF THE DRAWINGS

FIG. 5-$a$ is a diagram illustrating the structure of a lighting device for image capturing in the electronic component mounting apparatus according to the embodiment of the invention.

FIG. 5-*b* is a diagram illustrating the structure of a lighting device for image capturing in the electronic component mounting apparatus according to the embodiment of the invention.

FIG. 8-*a* is a diagram illustrating the dimensions of components of the lighting device for image capturing in the electronic component mounting apparatus according to the embodiment of the invention.

FIG. 8-*b* is a diagram illustrating the dimensions of components of the lighting device for image capturing in the electronic component mounting apparatus according to the embodiment of the invention.

FIG. 9-*a* is a diagram illustrating the dimensions of components of a lighting device for image capturing in an electronic component mounting apparatus according to the related art.

FIG. 9-*b* is a diagram illustrating the dimensions of components of a lighting device for image capturing in an electronic component mounting apparatus according to the related art.

BEST MODE FOR CARRYING OUT THE INVENTION

Hereinafter, exemplary embodiments of the invention will be described with reference to the accompanying drawings.

Figure 1:
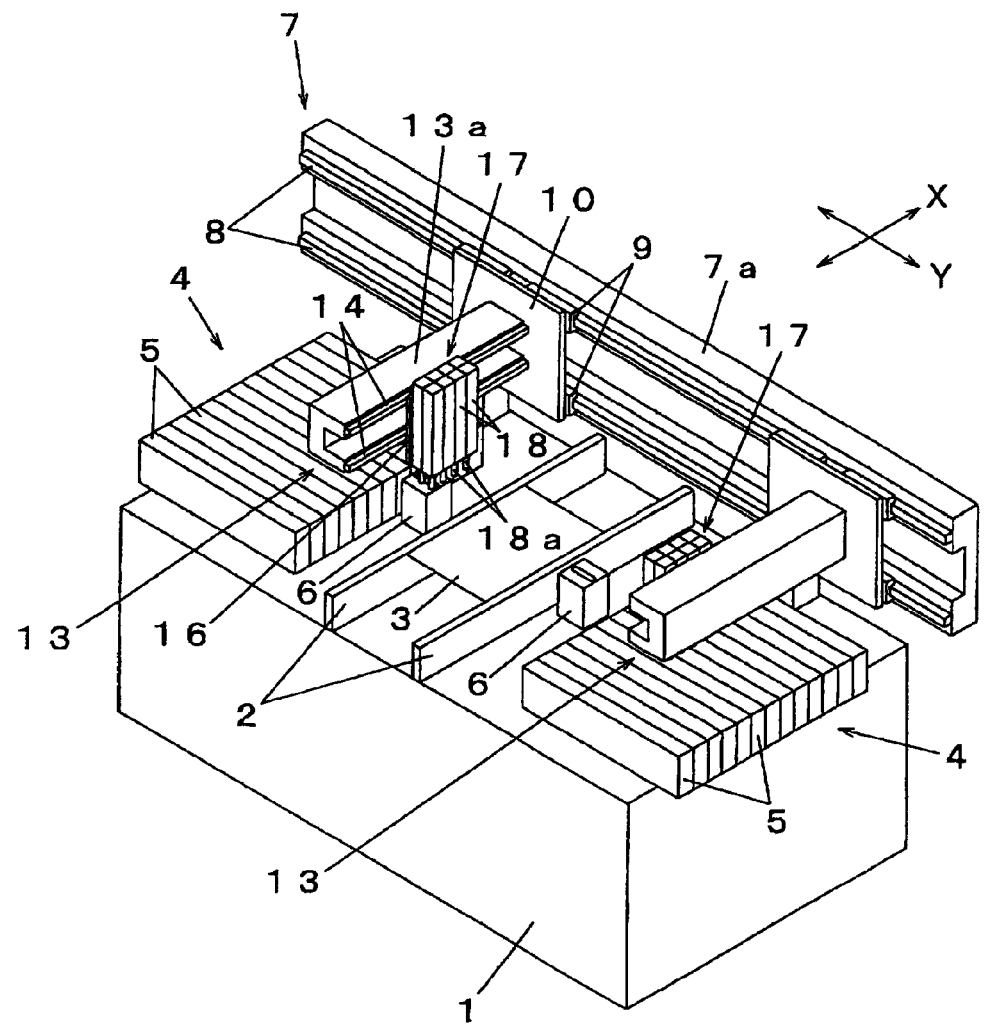
FIG. 1 is a perspective view illustrating an electronic component mounting apparatus according to an embodiment of the invention.
Figure 2:
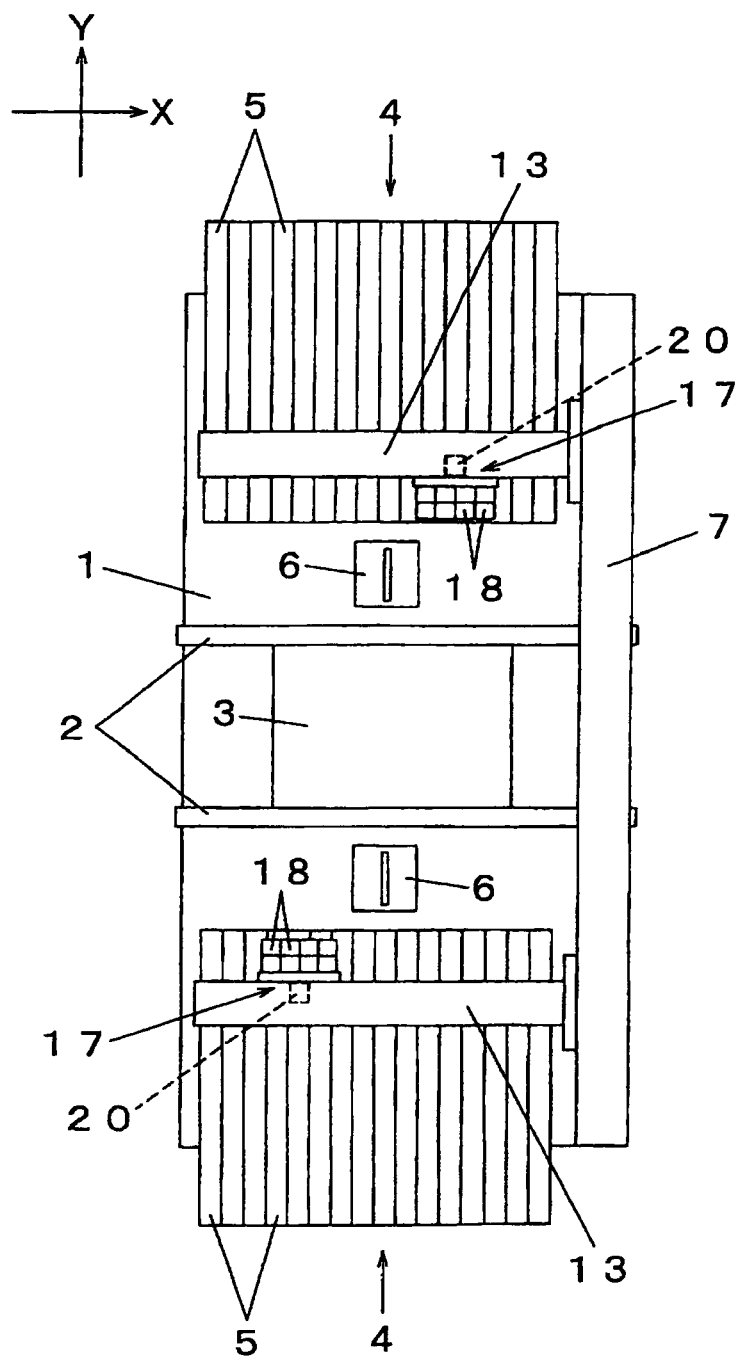
FIG. 2 is a plan view illustrating the electronic component mounting apparatus according to the embodiment of the invention.
Figure 3:
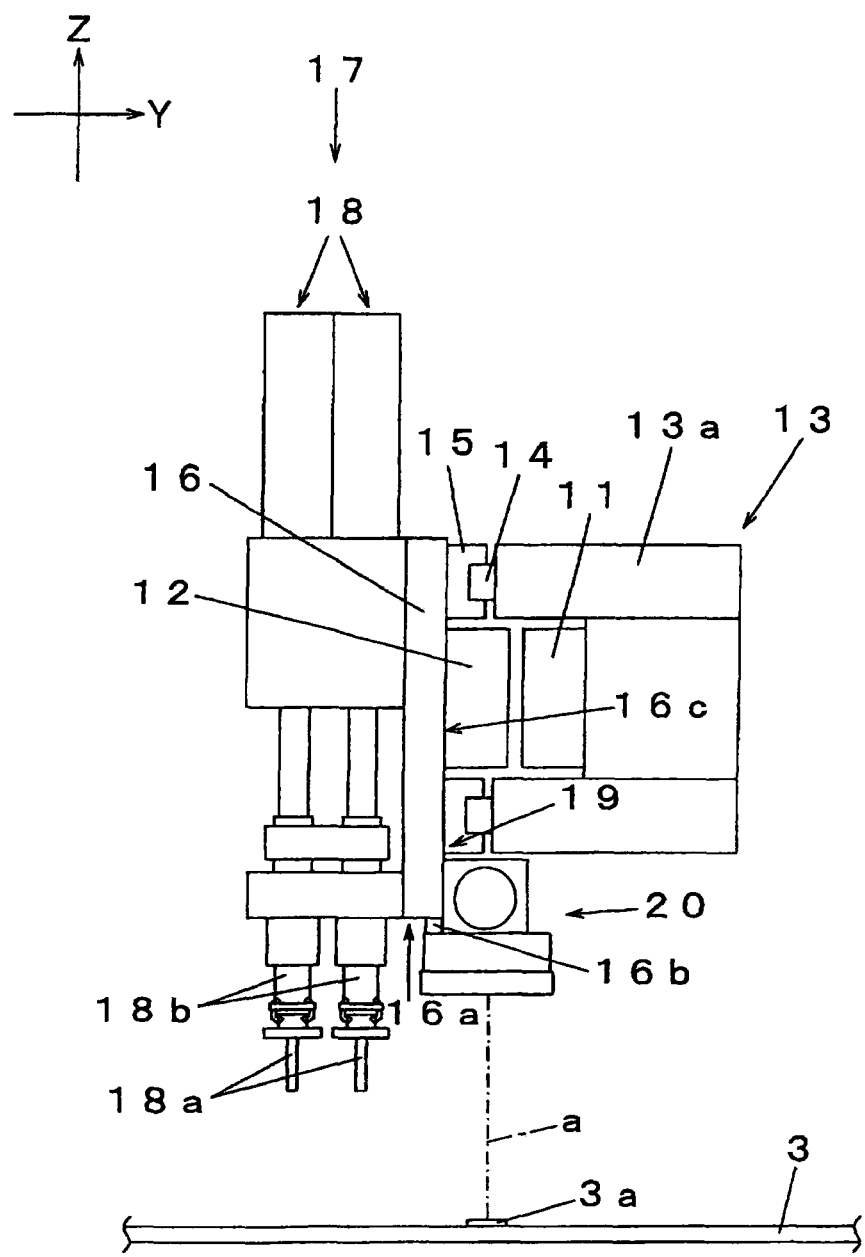
FIG. 3 is a side view illustrating a mounting head of the electronic component mounting apparatus according to the embodiment of the invention.

First, the structure of an electronic component mounting apparatus, serving as an electronic component placing apparatus that is used in an electronic component mounting line for mounting electronic components on a substrate, will be described with reference to FIGS. 1, 2, and 3. In FIG. 1, a transport path 2 is provided on a base 1 in an X direction. The transport path 2 transfers a substrate 3 to which electronic component are mounted, and positions the substrate 3 at a mounting location provided on the transport path 2. Part supply units 4 are provided at both sides of the transfer path 2, and a plurality of tape feeders 5 are mounted in each of the part supply units 4.

A Y-axis movement table 7 provided with a linear driving mechanism is disposed at one end of the base 1 in the X direction so as to be parallel to a Y direction. The Y-axis movement table 7 has as a main component a beam member 7*a* that is elongated in the horizontal direction, and linear rails 8 are provided on the beam member 7*a* in the horizontal direction. Linear blocks 9 are fitted to the linear rails 8 such that they can slide in the Y direction, and the linear blocks 9 are connected to an X-axis movement table 13 provided with a linear driving mechanism (see a fixed member 11 and a movable member 12 shown in FIG. 3), with a rectangular coupling bracket 10 provided in a vertical direction interposed therebetween.

The X-axis movement table 13 has as a main component a beam member 13*a* that is elongated in the X direction, and linear rails 14 are provided on the beam member 13*a* in the horizontal direction. As shown in FIG. 3, linear blocks 15 are fitted to the linear rails 14 such that they can slide in the X direction, and the linear rails 14 are connected to a mounting head 17 with a rectangular coupling bracket 16 provided in a vertical direction interposed therebetween. The coupling bracket 16 is coupled to the movable member 12 forming the linear driving mechanism, and the movable member 12 faces the fixed member 11 and slides thereon.

The mounting head 17 is a multiple-connected head including a plurality of unit mounting heads 18. A nozzle mounting portion 18*b* is provided in a lower part of each of the unit mounting heads 18, and a suction nozzle 18*a* that sucks and holds an electronic component is mounted in the nozzle mounting portion 18*b*. The suction nozzle 18*a* moves up and down by a nozzle lifting mechanism provided in the unit mounting head 18. The Y-axis movement table 7 and the X-axis movement table 13 are driven to move the mounting head 17 in the Y direction and the X direction, respectively. Then, the unit mounting heads 18 take out electronic components from the tape feeders 5 of the part supply units 4, and transport and load the electronic components on the substrate 3 that is positioned on the transport path 2.

A part recognizing device 6 is provided between the part supply unit 4 and the transport path 2. When the mounting head 17 that has taken out an electronic component from the part supply unit 4 moves above the part recognizing device 6, the part recognizing device 6 captures the image of the electronic component held in the mounting head 17 and recognizes the electronic component. When the electronic component is mounted on the substrate 3, the mounting position of the electronic component is corrected during the mounting of the electronic component on the basis of the result of the recognition. As shown in FIG. 2, a substrate recognizing camera unit 20 that is integrally moved with the mounting head 17 is attached to a lower part of the X-axis movement table 13. As shown in FIG. 3, the substrate recognizing camera unit 20 is attached to a camera mounting portion 19 that is provided in the coupling bracket 16, with its imaging optical axis a facing downward. The substrate recognizing camera unit 20 moves above the substrate 3 together with the mounting head 17 to capture the image of an identification mark 3*a* provided on the substrate 3.

Next, the structure of the camera mounting portion 19 attached to the mounting head 17 will be described with reference to FIG. 4. The camera mounting portion 19 is provided to attach the substrate recognizing camera unit 20 to the mounting head 17. In this embodiment, the camera mounting portion 19 is configured by providing the following parts in the coupling bracket 16 to which the mounting head 17 is coupled. In addition, the camera mounting portion 19 may be attached to other components except for the coupling bracket as long as they can integrally move with the mounting head 17. For example, the substrate recognizing camera unit 20 may be directly attached to the mounting head 17.

Figure 4:
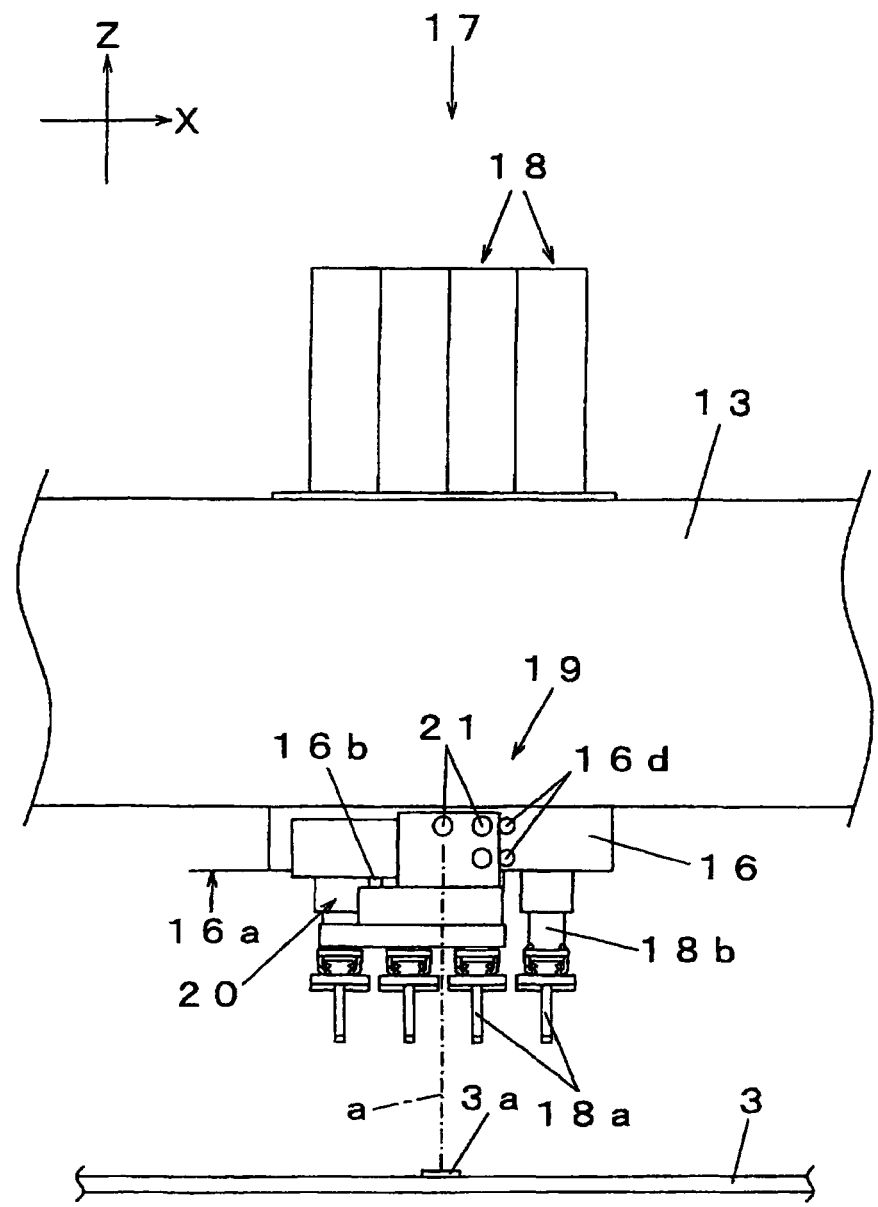
FIG. 4 is a rear view illustrating the mounting head of the electronic component mounting apparatus according to the embodiment of the invention.

FIG. 4 shows the rear side (which faces the X-axis movement table 13) of the mounting head 17. A positioning pin 16*b*, which is a reference point of the position of the substrate recognizing camera unit 20 in the Z direction, is provided in a lower surface 16*a* of the coupling bracket 16. In addition, two positioning pins 16*d*, which are reference points of the position of the substrate recognizing camera unit 20 in the X direction, is provided in a rear surface 16*c* of the coupling bracket 16. When the substrate recognizing camera unit 20 is attached to the camera mounting unit 19 with the coupling bracket 16 interposed therebetween, one side of the substrate recognizing camera unit 20 comes into contact with the positioning pin 16*d*, and the substrate recognizing camera unit 20 comes into contact with the positioning pin 16*b* provided in the lower surface 16*a*. In this state, the substrate recognizing camera unit 20 is tightened and fixed to the rear surface 16*c* of the coupling bracket 16 by bolts 21. In this way, the substrate recognizing camera unit 20 is positioned at a prescribed location in both the horizontal direction and the vertical direction with the imaging optical axis a aligned in the vertical direction.

Next, the structure of the substrate recognizing camera unit 20 will be described with reference to FIG. 5-a and FIG. 5-b. As shown in FIG. 5-a, the substrate recognizing camera unit 20 includes a camera 25, a coaxial lighting unit 26 that is coupled to a lower surface of the camera 25, and a surface lighting unit 30 that is mounted to a lower surface of the coaxial lighting unit 26. The camera 25 is configured by coupling a light receiving unit 23 having a light receiving element 23a provided therein to an optical unit 24 provided with lenses 24a and 24b and a prism 24c. The light receiving unit 23 is coupled to the optical unit 24 with the imaging optical axis a aligned in the horizontal direction. Therefore, image light that is vertically incident in the upward direction from the lower side through the lens 24b, which is close to an object whose image is to be captured, is refracted in the horizontal direction by the prism 24c and then incident on the light receiving element 23a through the lens 24a. Then, the light is focused on a predetermined position, and the image of the object whose image is to be captured is formed on the light receiving element 23a.

The coaxial lighting unit 26 includes a coaxial illumination light source portion 27 having a plurality of LEDs 28 and a half mirror 26a that reflects illumination light emitted from the coaxial illustration light source portion 27 downward. The reflected illumination light is incident on the substrate 3 in the vertical direction, and an object whose image is to be captured is illuminated in the coaxial direction of the imaging optical axis a. The surface lighting unit 30 is a lighting device for image capturing that emits illumination light to the substrate 3, which is an object whose image is to be captured by the camera 25, in the electronic component mounting apparatus, which is an electronic component placing apparatus. The surface lighting unit 30 includes as a main component a flat lighting substrate 31 having a light source portion 32 provided on a lower surface thereof.

The surface lighting unit 30 is disposed at a position that faces the substrate 3, which is an object whose image is to be captured, substantially in parallel to the substrate 3 in the state in which the substrate recognizing camera unit 20 having the surface light unit 30 provided therein captures the image of the substrate 3, which is an object whose image is to be captured. Therefore, in this state, the lighting substrate 31 is disposed substantially in parallel to the surface of the substrate 3 between the substrate 3 and the camera 25, and the light source portion 32 is provided on a lower surface of the lighting substrate facing the substrate 3. In the surface lighting unit 30 according to this embodiment, the light source portion 32 includes a plurality of light sources that can be individually controlled.

FIG. 5-b shows the structure of the light source portion 32 provided on the lower surface of the lighting substrate 31. Three kinds of individual light sources, that is, upper illumination light sources 32a, intermediate illumination light sources 32b, and lower illumination light sources 32c are arranged around an opening 31a. These individual light sources are all composed of LEDs. In this embodiment, LEDs emitting red light are used as the upper illumination light sources 32a and the intermediate illumination light sources 32b, and LEDs emitting white light are used as the lower illumination light sources 32c. The kind of LEDs used as these individual light sources are appropriately selected according to objects whose images are to be captured and the purpose of use.

As shown in FIG. 5-b, the upper illumination light sources 32a are arranged at the positions closest to the imaging optical axis a, and the intermediate illumination light sources 32b are arranged so as to surround the outside of the upper illumination light sources 32a. The lower illumination light sources 32c are arranged only at four corners of a rectangular range (which is represented by a dotted line A) having the imaging optical axis a as its center, outside the intermediate illumination light sources 32b. It is preferable that these individual light sources be arranged so as to be almost symmetric with respect to the imaging optical axis a.

Figure 6:
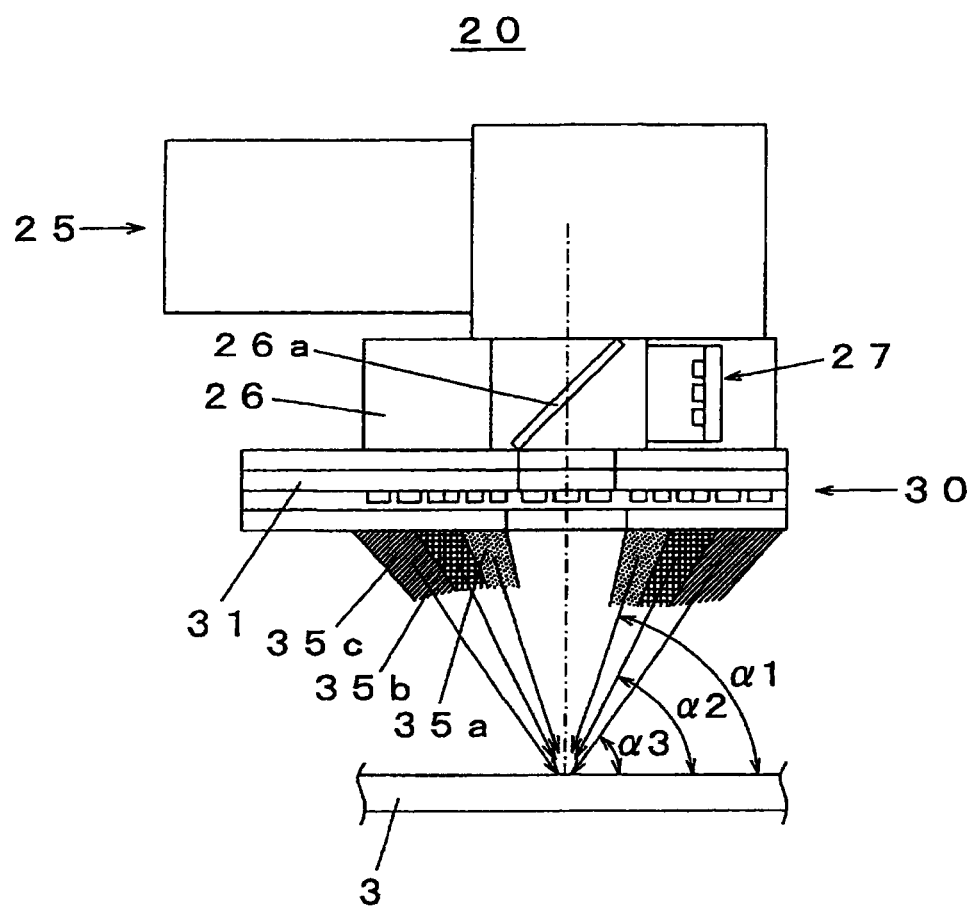
FIG. 6 is a diagram illustrating the emission angle of illumination light emitted from the lighting device for image capturing in the electronic component mounting apparatus according to the embodiment of the invention.

FIG. 6 shows the emission angle of illumination light, which is emitted downward from the surface lighting unit 30 provided on the lower surface of the lighting substrate 31, to the surface of the substrate 3, when the substrate recognizing camera unit 20 captures the image of the substrate 3. That is, as shown in FIG. 6, with the lighting unit 30 mounted in the substrate recognizing camera unit 20, the lighting substrate 31 is disposed substantially in parallel to the substrate 3. In this state, upper illumination light components 35a, intermediate illumination light components 35b, and lower illumination light components 35c respectively emitted from the upper illumination light sources 32a, the intermediate illumination light sources 32b, and the lower illumination light sources 32c are incident on the surface of the substrate 3 at emission angles of a1, a2, and a3, respectively. In addition, illumination light emitted from the coaxial illumination light source portion 27 is reflected from the half mirror 26a and then incident on the substrate 3 at an emission angle of 90 degrees.

Further, the reason why these individual light sources are divided into the upper, intermediate, and lower light sources is that three kinds of individual light sources, that is, the upper, intermediate, and lower light sources disposed at different positions in the height direction are needed to emit illumination light at different emission angles of a1, a2, and a3 from those in the lighting device according to the related art (see a lighting device 30A shown in FIG. 9-a). Therefore, in this embodiment, the light sources have only the same names as those in the related art. In addition, in this embodiment, the emission angles of a1, a2, and a3 mean the average emission angles of illumination light emitted from a plurality of LEDs forming the individual light sources.

In the arrangement of the individual light sources, the lower illumination light sources 32c, which are individual light sources that emit the lower illumination light component 35c (emission angle a1) having the smallest emission angle, are arranged only at four corners of the rectangular range having the imaging optical axis a as its center, as described above. In this arrangement, the point symmetry of illumination light incident on the substrate 3 is damaged a little, but the non-uniform distribution of illumination light is within an allowable range since the lower illumination light sources 32c are most distant from the imaging optical axis a, that is, the lower illumination light sources 32c have the longest illumination distance. The use of this arrangement makes it possible to considerably reduce the size of the surface light unit 30 in plan view and meet demands for a compact optical system, which will be described below.

Figure 7:
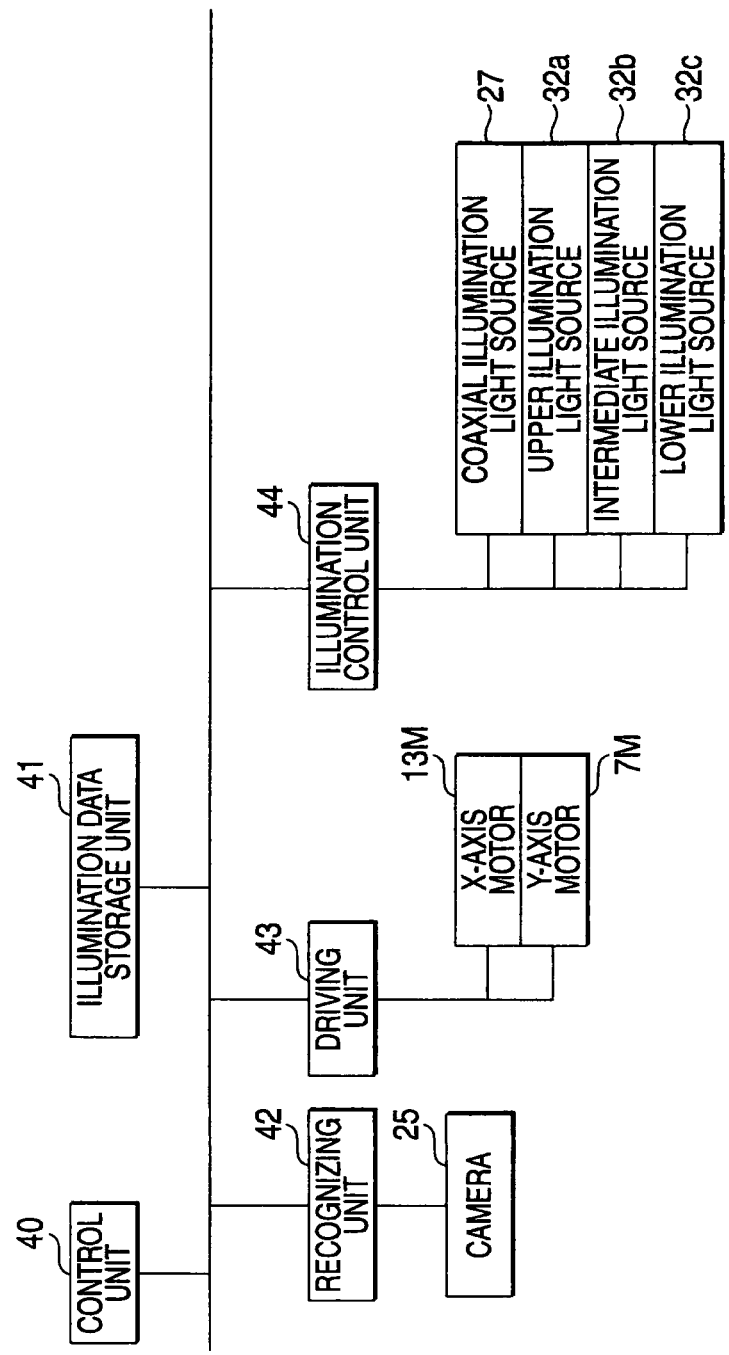
FIG. 7 is a block diagram illustrating the structure of a control system of the electronic component mounting apparatus according to the embodiment of the invention.

Next, the structure of a control system will be described with reference to FIG. 7. In FIG. 7, a control unit 40 is an overall control device provided with a CPU, and controls the following components. An illumination data storage unit 41 stores illumination data used to turn on the LEDs 28 of the coaxial illumination light source portion 27 or the individual light sources of the surface lighting unit 30 to illuminate the substrate 3, that is, data for the use of the individual light sources which are set for each object whose image is to be captured or data for the intensity of illumination light emitted from the individual light sources. A recognizing unit 42 recognizes image data acquired by the camera 25 and detects the position of the identification mark 3a. A driving unit 43 drives an X-axis linear motor 13M provided in the X-axis movement table 13 and a Y-axis linear motor 7M provided in the Y-axis movement table 7.

An illumination control unit 44 controls the upper illumination light sources 32a, the intermediate illumination light sources 32b, and the lower illumination light sources 32c, which are a plurality of individual light sources that emit illumination light components to the surface of the substrate 3 at different emission angles a1, a2, and a3, respectively. When the individual light sources are controlled by the illumination control unit 44, the illumination control unit 44 controls the individual light sources on the basis of the illumination data stored in the illumination data storage unit 41. That is, an illumination pattern, which is a combination of the on or off states of the individual light sources or illumination intensities, is set such that the best illumination state is obtained according to the purpose of recognition, the recognition type of image data, and surface characteristics of an object whose image is to be captured by the substrate recognizing camera unit 20.

Next, the effect of the substrate recognizing camera unit 20 provided with the surface lighting unit 30 having the above-mentioned structure will be described with reference to FIGS. 8-a, 8-b, 9-a and 9-b. FIGS. 8-a, 8-b, 9-a and 9-b are diagrams illustrating the substrate recognizing camera unit 20 provided with the surface lighting unit 30 according to this embodiment and a substrate recognizing camera unit 20A provided with a lighting unit 30A according to the related art, respectively.

The surface lighting unit 30 mounted to the substrate recognizing camera unit 20 is formed by arranging the upper illumination light sources 32a, the intermediate illumination light sources 32b, and the lower illumination light sources 32c shown in FIG. 5 on a single-plate lighting substrate 31. Therefore, as shown in FIG. 8-a, it is possible to considerably reduce the thickness T1 of the lighting unit 30. In contrast, as in the lighting unit 30A according to the related art that is mounted to the substrate recognizing camera unit 20A shown in FIG. 9-a, when three kinds of individual light sources, such as upper illumination light sources 36a, intermediate illumination light sources 36b, and lower illumination light sources 36c, are arranged in three layers in the vertical direction, the thickness T2 of the lighting unit 30A is the sum of the thicknesses of the individual light sources in the three layers. Therefore, the thickness T2 is several times larger than the thickness T1 shown in FIG. 8-a, which makes it difficult to reduce the dimensions of a lighting device in the height direction.

Further, in the surface lighting unit 30 according to this embodiment, as described above, in the arrangement of the upper illumination light sources 32a, the intermediate illumination light sources 32b, and the lower illumination light sources 32c, the lower illumination light sources 32c, which are light sources that emit the lower illumination light components 35c (emission angle a1) having the smallest emission angle, are arranged only at four corners of the rectangular range having the imaging optical axis a as its center. Therefore, as shown in FIG. 8-b, the lower illumination light sources 32c are arranged in a rectangular range having a length L and a width B. That is, the arrangement range of the lower illumination light sources 32c is the same as that obtained by cutting a portion of the arrangement range of the lower illumination light sources 36c shown in FIG. 9-a that protrudes in the width direction. In contrast, in the lighting unit 30A, as shown in FIG. 9-b, it is difficult to reduce the size of the lighting device in plan view to be smaller than the outside diameter D of a ring composed of the lower illumination light sources 36c. As a result, it is difficult to reduce the size of the lighting device in plan view.

As described above, in the surface lighting unit 30 according to this embodiment, a plurality of individual light sources that emit illumination light components to the surface of the substrate at different emission angles are arranged on a flat lighting substrate. In addition, among the individual light sources, the individual light sources that emit illumination light at the smallest emission angle are arranged only at four corners of a rectangular range having the imaging optical axis as its center.

In this way, it is possible to considerably reduce the thickness of the surface lighting unit 30, and prevent the individual light sources positioned in the outer circumference from protruding to the outside. As a result, it is possible to reduce the overall size of a lighting device in plan view. Therefore, in the present state in which the size of mounting equipment is being reduced with a decrease in the size of a substrate to which electronic components are mounted and an increase in the mounting density of electronic components, even when the dimensions of the mounting head in the height direction and the size thereof in plan view are restricted as compared to a mounting head according to the related art, the versatility of a lighting device for image capturing is ensured.

In the above-described embodiment, the surface lighting unit 30, serving as a lighting device for image capturing, is applied to the substrate recognizing camera unit of the electronic component mounting apparatus, but the invention is not limited thereto. The invention can be applied to various apparatuses in the field of mounting electronic components. For example, the invention can be applied to a part recognizing device of an electronic component mounting apparatus, a soldering examination device of a screen printing apparatus, and an image capturing device for examining the appearance of a substrate after parts are mounted.

Industrial Applicability

According to the invention, since a lighting device for image capturing used in an electronic component mounting apparatus has small dimensions in the height direction and a small size in plan view, it can meet demands for a reduction in size. In addition, the lighting device can be used for various apparatuses in the field of mounting electronic components, such as substrate recognizing cameras of electronic component mounting apparatuses.

The invention clamed is:

1. A lighting device for image capturing that emits illumination light to a substrate whose image is to be captured by a camera in an electronic component mounting apparatus, the lighting device comprising:
   a flat lighting substrate that is disposed between the substrate and the camera so as to be substantially parallel to the surface of the substrate, and has a light source portion provided on its one surface facing the substrate; and
   an illumination control unit that controls the light source portion,
   wherein the light source portion includes a plurality of individual light sources that are arranged around an opening for image capturing through which an imaging optical axis of the camera passes and emit the illumination light to the surface of the substrate at different emission angles, and the illumination control unit individually controls the plurality of individual light sources, wherein the flat lighting substrate has a rectangular range having four corners and the imaging optical axis as its center, wherein the plurality of individual light sources comprises a first group of light sources emitting the illumination light having the smallest emission angle among the individual light sources, a third group of light sources emitting the illumination light having the largest emission angle among the individual light sources, and a second group of light sources emitting the illumination light having an emission angle larger than the first group of light sources and smaller than the third group of light sources, and wherein the third group of light sources and the second group of light sources are arranged in concentric circles, the third group of light sources are arranged at positions closest to the imaging optical axis, the second group of light sources surround an outside of the third group of light sources, and the first group of light sources surround an outside of the second group of light sources and are arranged only in areas located between the concentric circle of the second group of light sources and the four corners of the rectangular range.

2. The lighting device for image capturing in the electronic component mounting apparatus according to claim 1,
wherein the illumination control unit controls the plurality of individual light sources on the basis of an illumination pattern obtained by combining the on or off states of the individual light sources or the illumination densities of light emitted from the individual light sources.

3. The lighting device for image capturing in the electronic component mounting apparatus according to claim 1,
wherein the individual light sources are LEDs.

4. The lighting device for image capturing in the electronic component mounting apparatus according to claim 1,
wherein the first group of light sources are LEDs that emit white light.

5. The lighting device for image capturing in the electronic component mounting apparatus according to claim 1,
wherein the first group of light sources are LEDs that emit white light, and the second and third groups of light sources are LEDs that emit red light.

* * * * *